United States Patent
Kondo et al.

(10) Patent No.: US 12,109,336 B2
(45) Date of Patent: Oct. 8, 2024

(54) SEALING AGENT FOR GENITALS

(71) Applicant: SANYO CHEMICAL INDUSTRIES, LTD., Kyoto (JP)

(72) Inventors: Eiji Kondo, Kyoto (JP); Hiroaki Maeda, Kyoto (JP); Shingo Kawabata, Kyoto (JP)

(73) Assignee: SANYO CHEMICAL INDUSTRIES, LTD., Kyoto (JP)

( * ) Notice: Subject to any disclaimer, the term of this patent is extended or adjusted under 35 U.S.C. 154(b) by 424 days.

(21) Appl. No.: 17/510,574

(22) Filed: Oct. 26, 2021

(65) Prior Publication Data
US 2022/0040386 A1    Feb. 10, 2022

Related U.S. Application Data

(62) Division of application No. 16/607,180, filed as application No. PCT/JP2018/017127 on Apr. 27, 2018, now abandoned.

(30) Foreign Application Priority Data

Apr. 28, 2017 (JP) ................. 2017-089424

(51) Int. Cl.
    A61L 31/14    (2006.01)
    A61L 31/06    (2006.01)
    C08G 18/10    (2006.01)
    C08G 18/77    (2006.01)

(52) U.S. Cl.
    CPC ........... *A61L 31/14* (2013.01); *A61L 31/06* (2013.01); *C08G 18/10* (2013.01); *C08G 18/77* (2013.01)

(58) Field of Classification Search
    CPC .. A61L 31/06; A61L 2400/06; A61L 2430/22; A61L 24/001; A61L 31/14; C08G 18/10; C08G 2190/00; C08G 18/4808; C08G 18/4825; C08G 18/4837; C08G 18/773; C09J 175/04
    See application file for complete search history.

(56) References Cited

U.S. PATENT DOCUMENTS

| 2005/0131192 A1 | 6/2005 | Matsuda et al. |
| 2014/0018510 A1* | 1/2014 | Kawakami ......... C08G 18/4837 528/73 |
| 2017/0036000 A1* | 2/2017 | Cline .................. A61M 31/00 |

FOREIGN PATENT DOCUMENTS

| EP | 1 741 454 | 1/2007 | |
| JP | 2002-516140 | 6/2002 | |
| WO | WO 99/60938 | * 12/1999 | ............. A61B 17/42 |
| WO | 03/051952 | 6/2003 | |

OTHER PUBLICATIONS

International Search Report issued Jun. 26, 2018 in International (PCT) Patent Application No. PCT/2018/017127.
Carnaghan et al., "Presealing of the chorioamniotic membranes prior to fetoscopic surgery: Preliminary study with unfertilised chicken egg models", European Journal of Obstetrics & Gynecology and Reproductive Biology, 2009, vol. 144, Suppl. 1, pp. S142-S145.
Roman et al., "Development of an implantable synthetic membrane for the treatment of preterm premature rupture of fetal membranes", Journal of Biomaterials Applications, 2016, vol. 30, No. 7, pp. 995-1003.
Sciscone et al., "Intracervical fibrin sealants: A potential treatment for early preterm premature rupture of the membranes", American Journal of Obstetrics & Gynecology, 2001, vol. 184, No. 3, pp. 368-373.
O'Brien et al., "An aggressive interventional protocol for early midtrimester premature rupture of the membranes using gelatin sponge for cervical plugging", American Journal of Obstetrics & Gynecology, 2002, vol. 187, No. 5, pp. 1143-1146.

* cited by examiner

*Primary Examiner* — Anna R Falkowitz
(74) *Attorney, Agent, or Firm* — WENDEROTH, LIND & PONACK, L.L.P.

(57) ABSTRACT

The present invention aims to provide a cervical canal sealant that can be used as a sealant to stop bleeding in the uterus and vaginal discharge, particularly, a cervical canal sealant that can block the cervical canal to inhibit amniotic fluid leakage and that can also be peeled off without damaging reproductive tissue. The present invention relates to a sealant for reproductive organs in which a cured product (X) at 25° C. has a storage modulus G' of 200 to 2,000 kPa, the cured product (X) being a cured product obtained by curing the sealant for reproductive organs to a thickness of 120 to 150 μm.

13 Claims, 1 Drawing Sheet

SEALING AGENT FOR GENITALS

TECHNICAL FIELD

The present invention relates to a sealant for reproductive organs.

BACKGROUND ART

Premature rupture of membrane occurs in 5 to 10% of all pregnancies, and about 20% thereof occurs during premature delivery (before 37 weeks of pregnancy). Premature delivery is the highest cause of newborn death and long-term serious sequelae. About one third of the causes of premature delivery before 37 weeks of pregnancy are related to premature rupture of membrane. Moreover, when premature rupture of membrane occurs during pregnancy around the limit of viability outside the body (5 to 7 months of pregnancy), and conditions without amniotic fluid or with amniotic fluid shortage persist, the fetus will have hypoplastic lung and the prognosis is poor. In addition, as the egg membrane, which is the ultimate barrier to keep the intrauterine environment sterile, is ruptured, infection will occur in the womb and interruption of pregnancy will be inevitable.

In regard to premature rupture of membranes in pregnancy, Non-Patent Literature 1 states that fibrin glue can contribute to a decrease in amniotic fluid leakage and an increase in the amniotic fluid index. Non-Patent Literature 2 states that use of a gelatin sponge can decrease amniotic fluid leakage.

CITATION LIST

Non-Patent Literature

Non-Patent Literature 1: American Journal of Obstetrics & Gynecology, 2001, 184(3), pp. 368 to 373
Non-Patent Literature 2: American Journal of Obstetrics & Gynecology, 2002, 187(5), pp. 1143 to 1146

SUMMARY OF INVENTION

Technical Problem

Yet, since the fibrin glue is a blood product, there is a risk of infection with a virus or the like, and thrombin contained in the fibrin glue unfortunately causes contraction of the uterus. The gelatin sponge may be sucked by the fetus and absorbed inside the body, causing problems such as intestinal obstruction.

The present invention aims to provide a sealant for reproductive organs that can be used as a sealant to stop bleeding in the uterus and vaginal discharge, particularly, a sealant for reproductive organs that can block the cervical canal to inhibit amniotic fluid leakage and that can also be peeled off without damaging reproductive tissue.

Solution to Problem

The present inventors conducted extensive studies to solve these problems, and completed the present invention.

Specifically, the present invention relates to a sealant for reproductive organs in which a cured product (X) at 25° C. has a storage modulus G' of 200 to 2,000 kPa, the cured product (X) being a cured product obtained by curing the sealant for reproductive organs to a thickness of 120 to 150 μm.

Advantageous Effects of Invention

The sealant for reproductive organs of the present invention can be used as a sealant to stop bleeding in the uterus and vaginal discharge. Particularly, the sealant for reproductive organs can block the cervical canal to inhibit amniotic fluid leakage and can also be peeled off without damaging reproductive tissue.

DESCRIPTION OF EMBODIMENTS

Figure 1A:
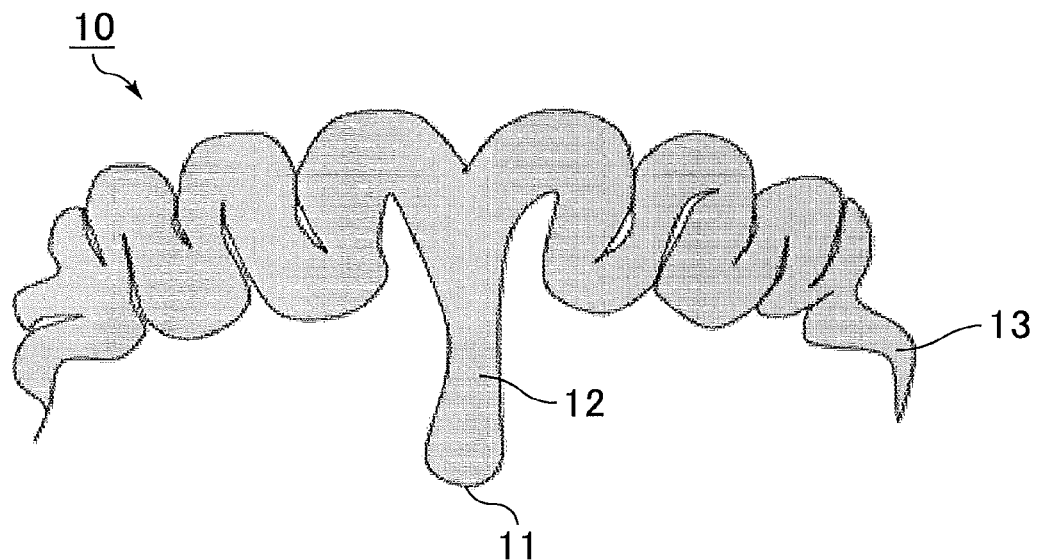
FIGS. 1A and 1B are schematic views showing an embodiment of a pressure-resistant sealing test that uses a porcine uterus.
Figure 1B:
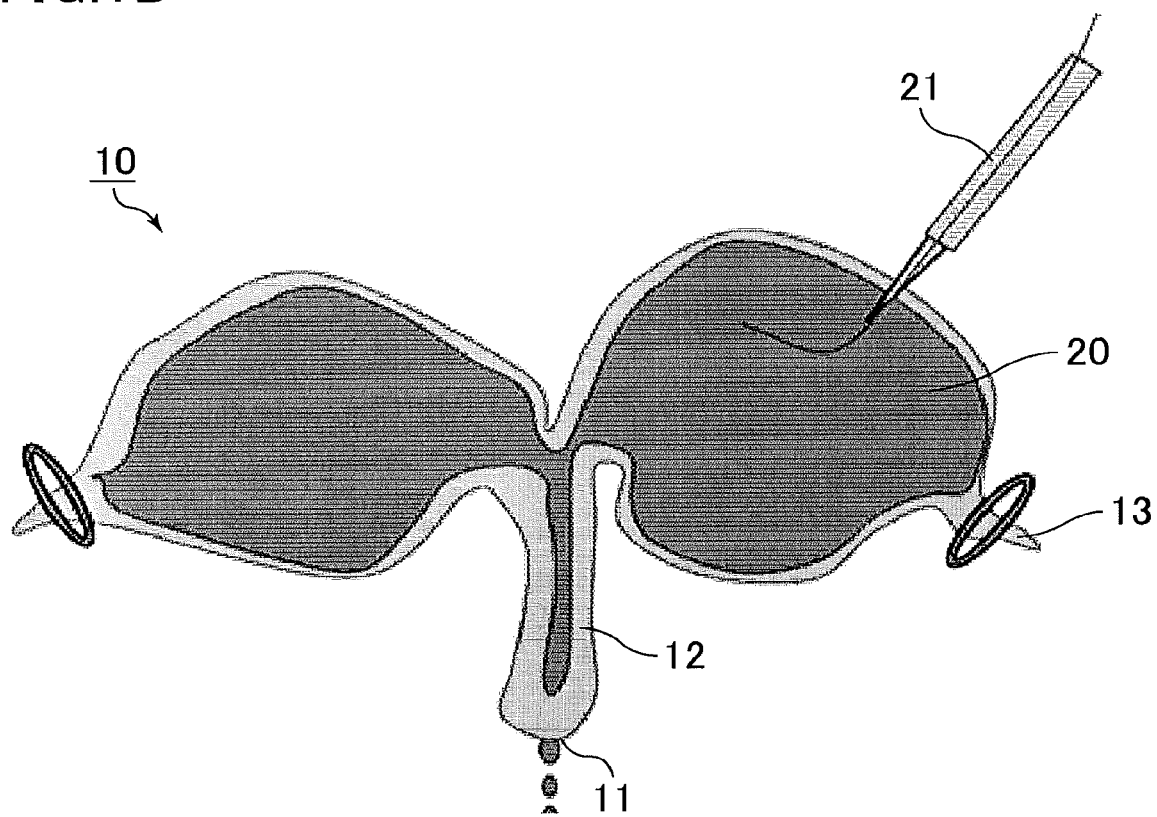

The present invention provides a sealant for reproductive organs in which the cured product (X) at 25° C. has a storage modulus G' of 200 to 2,000 kPa.

The storage modulus G' of the cured product (X) at 25° C. is preferably 250 to 1,900 kPa, more preferably 300 to 1,800 kPa.

A cured product having a storage modulus G' of less than 200 kPa has a low storage modulus and poor conformability to reproductive tissue. A cure product having a storage modulus G' of more than 2000 kPa has a hard coating and poor conformability to reproductive tissue.

Here, the cured product (X) which is a sample to be subjected to measurement of storage modulus and contact angle with water (described later) is a cured product obtained by curing the sealant for reproductive organs to a thickness of 120 to 150 μm.

The method of producing the cured product varies depending on the composition of the sealant for reproductive organs, but any method may be used as long as the cured product has a thickness of 120 to 150 μm.

When the sealant for reproductive organs of the present invention is liquid, the thickness of the cured product (X) refers to the coating thickness of the liquid sealant for reproductive organs. When the sealant for reproductive organs of the present invention is solid, the thickness of the cured product (X) refers to the average thickness of the solid sealant for reproductive organs as determined by measuring at ten positions with an equal interval using a pachymeter.

When the sealant for reproductive organs of the present invention is a sealant for reproductive organs containing an NCO-terminated urethane prepolymer (UP) that is a reaction product of a polyisocyanate component (A) and a polyol component (B) essentially containing a hydrophilic polyol (B1) (described later), specifically, the sealant used as a sample is obtained by placing a sealant for reproductive organs (about 1 g) on a glass plate (20 cm×26 cm), spreading the sealant to a coating thickness of 120 to 150 μm using a glass rod, curing the sealant by standing at a temperature of 25° C. and a relative humidity of 1 to 10% for 24 hours, and cutting the resulting cured product to a piece with a width of 5 to 8 mm and a length of 20 to 25 cm.

For the storage modulus G', a sample of the cured product (X) is measured to evaluate the storage modulus G' at 25° C., using a dynamic viscoelasticity measuring device (e.g., "Rheogel-E400" available from UBM) at a measurement temperature of −100° C. to 50° C., a heating rate of 2° C./rain, and a frequency of 11 Hz in a shear mode.

The composition of the sealant for reproductive organs of the present invention is not limited. For example, the composition may contain a urethane resin, an acrylic resin, a silicone resin, or the like.

Of these, the sealant for reproductive organs preferably contains a urethane resin in terms of flexibility and conformability to reproductive tissue. The sealant for reproductive organs more preferably contains an NCO-terminated urethane prepolymer (UP) that is a reaction product of a polyisocyanate component (A) and a polyol component (B) containing a hydrophilic polyol (B1), in terms of the curing speed.

In the sealant for reproductive organs of the present invention, preferably, the polyisocyanate component (A) contains a fluorine-containing non-aromatic polyisocyanate compound (A1), and the NCO-terminated urethane prepolymer (UP) has a fluorine content of 1 to 23 wt % based on the weight of the NCO-terminated urethane prepolymer (UP).

The sealant for reproductive organs of the present invention may also contain a fluorine atom-free polyisocyanate compound (A2), a fluorine-containing aromatic polyisocyanate compound (A3), and the like.

Examples of the fluorine-containing non-aromatic polyisocyanate compound (A1) include a C3-C24 fluorine-containing aliphatic diisocyanate (A11), a C8-C21 fluorine-containing alicyclic diisocyanate (A12), and a C9-C72 fluorine-containing poly- (tri- to hexavalent) isocyanate (A13).

Examples of the C3-C24 fluorine-containing aliphatic diisocyanate (A11) include those represented by OCN-Rf-NCO (Rf represents a C1-C22 perfluoroalkylene group) and those represented by OCN—CH$_2$—Rf-CH$_2$—NCO (Rf represents a C1-C20 perfluoroalkylene group).

Examples of those represented by OCN—Rf-NCO include difluoromethylene diisocyanate, perfluorodimethylene diisocyanate, perfluorotrimethylene diisocyanate, perfluorooctyl diisocyanate, and perfluoroeicosylene diisocyanate.

Examples of those represented by OCN—CH$_2$-Rf—CH$_2$—NCO include bis(isocyanatomethyl)difluoromethane, bis(isocyanatomethyl)perfluoroethane, bis(isocyanatomethyl)perfluoropropane, bis(isocyanatomethyl)perfluorobutane, bis(isocyanatomethyl)perfluoropentane, bis(isocyanatomethyl)perfluorohexane, and bis(isocyanatomethyl)perfluoroeicosane.

Examples of the C8-C21 fluorine-containing alicyclic diisocyanate (A12) include diisocyanatoperfluorocyclohexane, bis(isocyanatomethyl)perfluorocyclohexane, bis(isocyanatomethyl)perfluorodimethylcyclohexane, bis(isocyanatoperfluorocyclohexyl)perfluoropropane, bis(isocyanatomethylperfluorocyclohexyl)perfluoropropane, and bis(isocyanatomethylperfluorocyclohexyl)perfluoropentane.

Examples of the C9-C72 fluorine-containing poly-(tri- to hexavalent) isocyanate (A13) include isocyanurate compounds derived from the diisocyanates, adduct compounds derived from the diisocyanates, and tris(isocyanatotetrafluorocyclohexyl)methane.

The isocyanate group in the fluorine-containing non-aromatic polyisocyanate compound (A1) is present preferably at a position where there is less steric hindrance, more preferably a terminal position where there is less steric hindrance, in terms of reactivity with the polyol component (B) and the reactivity with blood or a body fluid, for example.

The fluorine-containing non-aromatic polyisocyanate compound (A1) may be a single compound or a mixture of two or more compounds.

The fluorine-containing non-aromatic polyisocyanate compound (A1) is preferably one having two isocyanate groups because a side reaction such as a crosslinking reaction is less likely to occur, for example.

In terms of safety against mutagenicity and the like, the fluorine-containing non-aromatic polyisocyanate compound (A1) is preferably the fluorine-containing aliphatic polyisocyanate (A11), more preferably a fluorine-containing aliphatic polyisocyanate represented by OCN—CH$_2$—Rf-CH$_2$—NCO or a fluorine-containing aliphatic polyisocyanate represented by OCN—Rf-NCO, still more preferably difluoromethylene diisocyanate, perfluorodimethylene diisocyanate, perfluorotrimethylene diisocyanate, perfluorooctyl diisocyanate, perfluoroeicosylene diisocyanate, bis(isocyanatomethyl)perfluoropropane, bis(isocyanatomethyl)perfluorobutane, bis(isocyanatomethyl)perfluoropentane, or bis(isocyanatomethyl)perfluorohexane.

Examples of the fluorine atom-free polyisocyanate compound (A2) include a C1-C24 fluorine atom-free aliphatic polyisocyanate (A21), a C8-C21 fluorine atom-free alicyclic polyisocyanate (A22), a C8-C21 fluorine atom-free araliphatic polyisocyanate (A23), a C8-C21 fluorine atom-free aromatic polyisocyanate (A24), and a modified compound (A25) of these.

Examples of the fluorine atom-free aliphatic polyisocyanate (A21) include tetramethylene diisocyanate, hexamethylene diisocyanate (hereinafter also referred to as "HDI"), 2,2,4-trimethylhexamethylene diisocyanate, and lysine diisocyanate.

Examples of the fluorine atom-free alicyclic polyisocyanate (A22) include isophorone diisocyanate (hereinafter also referred to as "IPDI"), dicyclohexylmethane-4,4'-diisocyanate (hereinafter also referred to as "hydrogenated MDI"), cyclohexylene diisocyanate, and methylcyclohexylene diisocyanate (hereinafter also referred to as "hydrogenated TDI").

Examples of the fluorine atom-free araliphatic polyisocyanate (A23) include m- or p-xylylene diisocyanate (hereinafter also referred to as "XDI") and α,α,α',α'-tetramethylxylylene diisocyanate (hereinafter also referred to as "TMXDI").

Examples of the fluorine atom-free aromatic polyisocyanate (A24) include 1,3- or 1,4-phenylene diisocyanate (hereinafter also referred to as "PDI"), 2,4- or 2,6-tolylene diisocyanate (hereinafter also referred to as "TDI"), 2,4'- or 4,4'-diphenylmethane diisocyanate (hereinafter also referred to as "MDI"), and crude MDI.

Examples of the modified compound (A25) of these include a urethane-modified compound, an isocyanurate-modified compound, an allophanate-modified compound, a biuret-modified compound, a uretdione-modified compound, a uretoneimine-modified compound, and a uretdione/isocyanurate-modified compound. Examples of modified compounds of HDI include urethane-modified HDI, carbodiimide-modified HDI, and trihydrocarbyl phosphate-modified HDI. Examples of modified compounds of MDI include urethane-modified MDI and carbodiimide-modified MDI. Examples of modified compounds of TDI include urethane-modified TDI and carbodiimide-modified TDI.

The fluorine atom-free polyisocyanate compound (A2) may be a single compound or a mixture of two or more compounds.

In terms of reactivity and the like, the polyisocyanate compound (A2) is preferably the fluorine atom-free aromatic polyisocyanate (A24), more preferably MDI or TDI.

In terms of safety, the polyisocyanate compound (A2) is preferably a fluorine atom-free aliphatic polyisocyanate (A21), more preferably HDI.

When the fluorine atom-free polyisocyanate compound (A2) is used, in terms of safety against mutagenicity and the like, the (A2) content (wt %) is preferably 0.1 to 20, more preferably 0.2 to 10, still more preferably 0.3 to 5 based on the weight of the fluorine-containing non-aromatic polyisocyanate compound (A1).

Examples of the fluorine-containing aromatic polyisocyanate compound (A3) include a fluorine-containing aromatic polyisocyanate obtained by replacing some or all the hydrogen atoms in the aromatic ring of the fluorine atom-free aromatic polyisocyanate (A24) by fluorine atoms.

A fluorine-containing aromatic polyisocyanate (A31) is obtained by replacing all the hydrogen atoms in the aromatic ring by fluorine atoms. Specific examples include 1,3- or 1,4-perfluorophenylene diisocyanate, 3,5,6- or 3,4,5-trifluoro-2,4- or 2,6-tolylene diisocyanate, and tetrafluoro-2,4'- or 4,4'-diphenylmethane diisocyanate.

A fluorine-containing aromatic polyisocyanate (A32) is obtained by replacing some hydrogen atoms in the aromatic ring by fluorine atoms. Specific examples include trifluoromethyl-monofluoro-phenylene-1,3-diisocyanate, trifluoromethyl-monofluoro-phenylene-1,4-diisocyanate, and 2,4'- or 4,4'-diphenyldifluoromethane diisocyanate.

A fluorine-containing aromatic polyisocyanate (A33) is obtained by replacing all the hydrogen atoms by fluorine atoms. Specific examples include 2,4-perfluorotolylene diisocyanate, 2,6-perfluorotolylene diisocyanate, 2,4'-perfluorodiphenylmethane diisocyanate, and 4,4'-perfluorodiphenylmethane diisocyanate.

The fluorine-containing aromatic polyisocyanate compound (A3) may be a single compound or a mixture of two or more compounds.

In terms of reactivity and the like, the fluorine-containing aromatic polyisocyanate compound (A3) is preferably the fluorine-containing aromatic polyisocyanate (A31) or the fluorine-containing aromatic polyisocyanate (A33) in which at least one or all the hydrogen atoms in the aromatic ring are replaced by fluorine atoms, with the fluorine-containing aromatic polyisocyanate (A33) being more preferred.

When the fluorine-containing aromatic polyisocyanate compound (A3) is used, in terms of safety against mutagenicity and the like, the (A3) content (wt %) is preferably 0.1 to 5, more preferably 0.2 to 3, still more preferably 0.3 to 2 based on the weight of the fluorine-containing non-aromatic polyisocyanate compound (A1).

In the present invention, the polyol component (B) contains the hydrophilic polyol (B1) and may also contain another polyol (B2) having low hydrophilicity.

Preferably, the hydrophilic polyol (B1) is a polyol containing an oxyethylene group and having an oxyethylene unit content of 30 to 90 wt % based on the weight of the hydrophilic polyol (B1). The hydrophilic polyol (B1) can be a polyether polyol (B11) containing an oxyethylene group, a polyester polyol (B12) obtained from the polyether polyol (B11), or the like.

The HLB of the hydrophilic polyol (B1) is preferably 4 to 20, more preferably 4.5 to 20, in terms of reactivity and adhesive strength to reproductive tissue.

The "HLB" is an indicator that indicates the hydrophilic-lipophilic balance. The HLB value can be calculated from a ratio of the organicity value and the inorganicity value of an organic compound by, for example, the Oda method described in Kaimen kasseizai nyumon (Introduction to Surfactants) (Takehiko Fujimoto, published by Sanyo Chemical Industries, Ltd. 2007), p. 212. HLB≈10×inorganicity/organicity The organicity and inorganicity values to determine the HLB can be calculated using values listed in the table on page 213 in Kaimen kasseizai nyumon.

Examples of the polyether polyol (B11) containing an oxyethylene group include an ethylene oxide adduct to a compound having at least two active hydrogen atoms, and a coadduct of ethylene oxide and C3-C8 alkylene oxide (such as 1,2- or 1,3-propylene oxide, 1,2-, 1,3-, 2,3- or 1,4-butylene oxide, or styrene oxide) to the compound having at least two active hydrogen atoms. In the case of the coadduct, the addition mode may be any of random, block, or a combination of random and block. Yet, in terms of adhesive strength to reproductive tissue, random addition is preferred.

The C3-C8 alkylene oxide is preferably 1,2-propylene oxide in terms of adhesive strength to reproductive tissue. The simple term "propylene oxide" described below refers to "1,2- or 1,3-propylene oxide".

Examples of the compound having at least two active hydrogen atoms include water, diols, trihydric to octahydric polyols, dicarboxylic acids, trivalent to tetravalent polycarboxylic acids, monoamines, polyamines, and polythiols.

When a compound having two active hydrogen atoms is used, a hydrophilic diol is obtained. When a compound having three or more active hydrogen atoms is used, a trihydric or higher hydric hydrophilic polyol is obtained.

Examples of the diols include C2-C30 alkylene glycols (such as ethylene glycol, propylene glycol, trimethylene glycol, 1,4-butanediol, 1,6-hexanediol, octane diol, decane diol, dodecane diol, tetradecane diol, neopentyl glycol, and 2,2-diethyl-1,3-propanediol); C6-C24 alicyclic diols (such as 1,4-cyclohexane dimethanol and hydrogenated bisphenol A); C15-C30 bisphenols (such as bisphenol A, bisphenol F, and bisphenol S); dihydroxybenzenes (such as catechol and hydroquinone).

Examples of the trihydric to octahydric polyols include C3-08 aliphatic polyhydric alcohols (such as glycerin, trimethylolethane, trimethylolpropane, pentaerythritol, sorbitan, diglycerin, and sorbitol).

Examples of the dicarboxylic acids include C4-C32 alkane dicarboxylic acids (such as succinic acid, adipic acid, sebacic acid, azelaic acid, sebacic acid, dodecane dicarboxylic acid, octadecane dicarboxylic acid, dodecyl succinic acid, and octadecyl succinic acid); C4-C32 alkene dicarboxylic acids (such as maleic acid, fumaric acid, citraconic acid, mesaconic acid, dimer acid, dodecenyl succinic acid, and pentadecenyl succinic acid); and C8-C20 aromatic dicarboxylic acids (such as phthalic acid, isophthalic acid, terephthalic acid, and naphthalene dicarboxylic acid). In addition, acid anhydrides of dicarboxylic acids (such as maleic anhydride and phthalic anhydride) and lower alkyl (C1-C4) esters (such as methyl ester, ethyl ester, isopropyl ester, and t-butyl ester) can also be used.

Examples of the trivalent and tetravalent polycarboxylic acids include C9-C20 aromatic polycarboxylic acids (such as trimellitic acid and pyromellitic acid). In addition, acid anhydrides of polycarboxylic acids (such as trimellitic anhydride and pyromellitic anhydride) and lower alkyl (C1-04) esters (such as methyl ester, ethyl ester, and isopropyl ester) can also be used.

Examples of the monoamines include ammonia and C1-C20 aliphatic primary amines (e.g., C1-C20 alkyl amines (such as methylamine, ethylamine, propylamine, hexylamine, dodecylamine, and eicosylamine)); C4-C15 alicyclic amines (such as piperidine, aminocyclohexane, isophorone monoamine, and 4-methylene dicyclohexane monoamine); and C6-C15 aromatic ring-containing aliphatic amines (such as benzylamine).

Examples of the polyamines include C2-C18 aliphatic polyamines (e.g., C2-C12 alkylene diamines (such as ethylenediamine, propylenediamine, trimethylenediamine, hexamethylenediamine, N,N'-diethylethylenediamine, and undecylenediamine) and polyalkylene (C2-C6) polyamines (such as diethylenetriamine, dipropylenetriamine, triethylenetetramine, and pentaethylenenhexamine)); C4-C15 alicyclic polyamines (such as 1,3-diaminocyclohexane, isophoronediamine, and 4,4'-methylenedicyclohexanediamine); and C4-C15 heterocyclic polyamines (such as piperazine, N-aminoethylpiperazine, 1,4-diaminoethylpiperazine, and N-aminoethylpyridine).

Examples of the polythiols include C2-C24 dithiols (such as ethanedithiol, 1,4-butanedithiol, and 1,6-hexanedithiol), trivalent to hexavalent C5-03000 polythiols (such as "Capcure 3800" (product name, available from Japan Epoxy Resins Co., Ltd.) and polyvinylthiol).

Examples of the compound having at least two active hydrogen atoms also include amino acids, oxycarboxylic acids, and amino alcohols, in addition to those mentioned above.

The compound having at least two active hydrogen atoms may be a single compound or a mixture of two or more compounds.

The compound having at least two active hydrogen atoms is preferably water or a diol, more preferably water or a C2-C30 alkylene glycol, still more preferably water or a C2-C4 alkylene glycol, in terms of safety to living organisms and adhesive strength to reproductive tissue.

Preferred examples of the polyether polyol (B11) containing an oxyethylene group include ethylene oxide adducts to a diol (such as an ethylene oxide adduct to ethylene glycol and an ethylene oxide adduct to propylene glycol) and coadducts of ethylene oxide and C3-C8 alkylene oxide to a diol (such as a random or block coadduct of ethylene oxide and propylene oxide to ethylene glycol, and a random or block coadduct of ethylene oxide and butylene oxide to ethylene glycol).

The polyether polyol (B11) containing an oxyethylene group is preferably an ethylene oxide adduct to a diol or a coadduct of ethylene oxide and propylene oxide to a diol, with the coadduct of ethylene oxide and propylene oxide to a diol being more preferred, in order to increase reactivity with water and further improve adhesive strength to reproductive tissue and the like.

The polyether polyol (B11) containing an oxyethylene group may be a single compound or a mixture of two or more compounds.

The polyether polyol (B11) containing an oxyethylene group has a hydroxyl group equivalent (the number average molecular weight per hydroxyl group) of preferably 50 to 5000, more preferably 100 to 4000, still more preferably 200 to 3000. With these ranges, properties such as adhesive strength to reproductive tissue are further improved.

The hydroxyl group equivalent is measured in accordance with JIS K 1557-1:2007.

The polyester polyol (B12) obtained from the polyether polyol (B11) containing an oxyethylene group is preferably a polyester polyol obtained from the polyether polyol (B11) containing an oxyethylene group and a compound having at least two active hydrogen atoms (examples include polyesters from the dicarboxylic acid, the acid anhydride of the dicarboxylic acid, and/or the dicarboxylic acid lower alkyl ester mentioned above). These polyesters are preferably terminated with a hydroxyl group.

The compound having at least two active hydrogen atoms can also be a polycarboxylic acid, an acid anhydride of a polycarboxylic acid, or a polycarboxylic acid lower alkyl ether. When these compounds are used, the amount of these compounds (mol %) is preferably 0.1 to 10 mol %, more preferably 0.1 to 5 mol %, still more preferably 0.1 to 2 mol % based on the total number of moles of all the compounds having at least two active hydrogen atoms that were used. With these ranges, properties such as adhesive strength to reproductive tissue are further improved.

Preferred examples of the polyester polyol (B12) include polyester diols obtained from the compounds mentioned as preferred examples of the polyether polyol (B11) containing an oxyethylene group and dicarboxylic acids (such as adipic acid, sebacic acid, maleic acid, and phthalic acid) or anhydrides of dicarboxylic acids and/or dicarboxylic acid lower alkyl esters (such as methyl or ethyl esters of dicarboxylic acids).

Of these, in terms of adhesive strength to reproductive tissue and the like, the polyester polyol (B12) is preferably a polyester diol obtained from an ethylene oxide adduct to a diol and a dicarboxylic acid or an acid anhydride of a dicarboxylic acid and/or a dicarboxylic acid lower alkyl ester; a polyester diol obtained from a random or block coadduct of ethylene oxide and propylene oxide to a diol and a dicarboxylic acid or an acid anhydride of a dicarboxylic acid and/or a dicarboxylic acid lower alkyl ester. The polyester diol obtained from an ethylene oxide adduct to a diol and a dicarboxylic acid or an acid anhydride of a dicarboxylic acid and/or a dicarboxylic acid lower alkyl ester is more preferred.

Each of these polyester polyols (B12) may be a single compound or a mixture of two or more compounds.

The polyester polyol (B12) has a hydroxyl group equivalent of preferably 50 to 5000, more preferably 100 to 4000, still more preferably 200 to 3000. With these ranges, properties such as adhesive strength to reproductive tissue are further improved.

The hydrophilic polyol (B1) may be a single compound or a mixture of two or more compounds.

The hydrophilic polyol (B1) is preferably the polyether polyol (B11) containing an oxyethylene group in order to increase reactivity with water and further improve adhesive strength to reproductive tissue and the like. The hydrophilic polyol (B1) is more preferably an ethylene oxide adduct to a diol or a coadduct of ethylene oxide and propylene oxide to a diol, still more preferably a coadduct of ethylene oxide and propylene oxide to a diol.

The hydrophilic polyol (B1) has an oxyethylene unit content of preferably 30 to 90 wt %, more preferably 40 to 90 wt %, still more preferably 50 to 90 wt % based on the weight of the hydrophilic polyol (B1). With these ranges, properties such as adhesive strength to reproductive tissue are further improved.

Examples of the other polyol (B2) having low hydrophilicity include the diols and the trihydric to hexahydric polyols mentioned above as the compounds having at least two active hydrogen atoms. Other examples include a polyether polyol (B21) containing an oxyalkylene unit and having an oxyethylene unit content of less than 30 wt % based on the weight of the polyol (B2).

Examples of the other polyol (B2) can also be a polyester polyol (B22) obtained from the polyether polyol (B21) or a polyester polyol (B23) not containing an oxyethylene group or a C3-C8 oxyalkylene group.

Examples of the polyether polyol (B21) include a (co) adduct of C3-C8 alkylene oxide to the compound having at least two active hydrogen atoms, and a coadduct of ethylene oxide and C3-C8 alkylene oxide to the compound having at least two active hydrogen atoms. Yet, the oxyethylene unit content is less than 30 wt % based on the weight of the polyol (B2).

Preferred examples of the polyether polyol (B21) include polypropylene glycol (a propylene oxide adduct to propylene glycol), an ethylene oxide adduct to polyalkylene glycol (such as a block adduct of ethylene oxide and propylene oxide to ethylene glycol or propylene glycol, having an oxyethylene unit content of 5 wt % or more and less than 30 wt %), a random copolymer of propylene oxide and ethylene oxide (such as a random adduct of ethylene oxide and propylene oxide to ethylene glycol or propylene glycol, having an oxyethylene unit content of 10 to 25 wt %), polytetramethylene glycol (a 1,2-, 1,3-, 2,3-, or 1,4-butylene oxide adduct to 1,4-butylene glycol), and a copolymer of 1,4-butylene oxide and ethylene oxide (such as a block or random adduct of 10 to 25 wt % of ethylene oxide and 75 to 90 wt % of 1,4-butylene oxide to ethylene glycol or butylene glycol, having an oxyethylene unit content of 10 to 25 wt %).

Of these, in terms of adhesion to reproductive tissue and the like, an ethylene oxide adduct to polypropylene glycol (such as one having an oxyethylene unit content or 5 wt % or more and less than 30 wt %) is preferred, and an ethylene oxide adduct to polypropylene glycol (such as one having an oxyethylene unit content of 15 wt % or more and less than 30 wt %) is more preferred.

Each of these polyether polyols (B21) may be a single compound or a mixture of two or more compounds.

A preferred range of the hydroxyl group equivalent of the polyether polyol (B21) is the same as that of the polyether polyol (B11).

Examples of the polyester polyol (B22) obtained from the polyether polyol (B21) include polyester polyols that can be derived from the polyether polyol (B21) and the dicarboxylic acids, the acid anhydrides of the dicarboxylic acids, or the dicarboxylic acid lower alkyl esters mentioned above as examples of the compound having at least two active hydrogen atoms.

Preferred examples of the polyester polyol (B22) include polyester polyols (having an oxyethylene unit content of less than 30 wt %) that can be derived from the following component(s): polypropylene glycol (a propylene oxide adduct to propylene glycol); an ethylene oxide adduct to polyalkylene glycol (such as a block adduct of ethylene oxide and propylene oxide to ethylene glycol or propylene glycol, having an ethylene oxide content of 5 wt % or more and less than 30 wt %); a random copolymer of propylene oxide and ethylene oxide (such as a random adduct of ethylene oxide and propylene oxide to ethylene glycol or propylene glycol, having an ethylene oxide content of 10 to 25 wt %); polytetramethylene glycol (a 1,2-, 1,3-, 2,3-, or 1,4-butylene oxide adduct to 1,4-butylene glycol); and/or a copolymer of 1,4-butylene oxide and ethylene oxide (such as a block or random adduct of 10 to 25 wt of ethylene oxide and 75 to 90 wt % of 1,4-butylene oxide to ethylene glycol or butylene glycol, having an ethylene oxide content of 10 to 25 wt %), and the following component(s): dicarboxylic acids (such as adipic acid, sebacic acid, maleic acid, and phthalic acid); acid anhydrides of dicarboxylic acids; and/or dicarboxylic acid lower alkyl esters (such as methyl ester and ethyl ester of dicarboxylic acids).

Each of these polyester polyols (B22) may be a single compound or a mixture of two or more compounds.

Examples of the polyester polyol (B23) not containing an oxyethylene group or a C3-C8 oxyalkylene group include polyesters that can be derived from the diols and/or trihydric to hexahydric polyols and the dicarboxylic acids, the acid anhydrides of the dicarboxylic acids, and/or the dicarboxylic acid lower alkyl esters; and polyester that can be derived from ring-opening polymerization of caprolactone.

Preferred examples of the polyester polyol (B23) include polyester diols derived from butanediol and adipic acid; polyester diols derived from ethylene glycol and adipic acid; polyester diols derived from hexamethylene glycol and adipic acid; polyester diols derived from ethylene glycol, butanediol, and adipic acid; polyester diols derived from ethylene glycol and sebacic acid; polyester diol derived from cyclohexane diol and phthalic acid; and polycaprolactone derived from ring-opening polymerization of caprolactone.

Each of these polyester polyols (B23) may be a single compound or a mixture of two or more compounds.

Of these, in terms of adhesive strength to reproductive tissue and the like, the other polyol (B2) having low hydrophilicity is preferably the polyether polyol (B21) having an oxyethylene unit content of less than 30 wt % on the weight basis, more preferably polypropylene glycol or an adduct of ethylene oxide in an amount of 15 wt % or more and less than 30 wt % to polypropylene glycol, still more preferably polypropylene glycol.

The polyol component (B) has an oxyethylene unit content of preferably 30 to 90 wt %, more preferably 35 to 90 wt %, still more preferably 40 to 90 wt %, particularly preferably 50 to 90 wt % based on the weight of the polyol component (B). With these ranges, properties such as adhesive strength to reproductive tissue are further improved.

The polyol component (B) has an average hydroxyl group equivalent of preferably 50 to 5000, more preferably 100 to 4000, still more preferably 200 to 3000. With these ranges, properties such as adhesive strength to reproductive tissue are further improved.

The polyol component (B) as a whole has a number average molecular weight of preferably 100 to 10000, more preferably 200 to 8000. With these ranges, the cured product of the sealant for reproductive organs has good flexibility and adequate adhesion to reproductive tissue.

In the present invention, the number average molecular weight (Mn) is measured by gel permeation chromatography (GPC) using polyoxyethylene glycol as a standard substance.

Device: gel permeation chromatography
Solvent: THF
Sample concentration: 0.25 wt %
Column stationary phase: TSKgel SuperH4000
Column temperature: 40° C.

When the hydrophilic polyol (B1) and the other polyol (B2) having low hydrophilicity are used in combination, the hydrophilic polyol (B1) is preferably the polyether polyol (B11); more preferably an ethylene oxide adduct to a diol (such as an ethylene oxide adduct to ethylene glycol or an ethylene oxide adduct to propylene glycol) or a coadduct of ethylene oxide and C3-C8 alkylene oxide to a diol (such as a random or block coadduct of ethylene oxide and propylene oxide to ethylene glycol, or a random or block coadduct of ethylene oxide and butylene oxide to ethylene glycol); still more preferably a coadduct of ethylene oxide and propylene oxide to a diol; particularly preferably a random coadduct of ethylene oxide and propylene oxide to a diol.

When the hydrophilic polyol (B1) and the other polyol (B2) having low hydrophilicity are used in combination, the other polyol (B2) having low hydrophilicity is preferably, in addition to a diol or a trihydric to hexahydric polyol, a polyether polyol having an oxyethylene unit content of less than 30 wt % based on the weight of the other polyol (B2) having low hydrophilicity; more preferably a polyether polyol containing an oxypropylene group and having an oxyethylene unit content of less than 30 wt % based on the weight of the other polyol (B2) having low hydrophilicity; still more preferably polypropylene glycol.

When the hydrophilic polyol (B1) and the other polyol (B2) having low hydrophilicity are used in combination, in terms of adhesion to reproductive tissue, the polyol component (B) is preferably a mixture of the polyether polyol (B11) as the hydrophilic polyols (B1) and the polyether polyol, as the other polyols (B2) having low hydrophilicity, which has an oxyethylene unit content of less than 30 wt % based on the weight of the other polyol (B2) having low hydrophilicity. The polyol component (B) is more preferably a mixture of a coadduct of ethylene oxide and propylene oxide to a diol as the hydrophilic polyol (B1) and the polyether polyol, as the other polyol (B2) having low hydrophilicity, which contains an oxypropylene unit and has an oxyethylene unit content of less than 30 wt % based on the weight of the other polyol (B2) having low hydrophilicity. The polyol component (B) is still more preferably a mixture of a random coadduct of ethylene oxide and propylene oxide to a diol as the hydrophilic polyol (B1) and the polypropylene glycol as the other polyol (B2) having low hydrophilicity.

When the hydrophilic polyol (B1) and the other polyol (B2) having low hydrophilicity are used in combination, the polyol component (B) has a hydrophilic polyol (B1) content of preferably 20 to 99 wt %, more preferably 30 to 95 wt % based on the weight of the polyol component (B), in terms of adhesion to reproductive tissue.

The polyol component (B) has a (B2) content (wt %) (the amount of the other polyol (B2) having low hydrophilicity) of preferably 1 to 80 wt %, more preferably 5 to 70 wt % based on the weight of the polyol component (B), in terms of adhesion to reproductive tissue.

The NCO-terminated urethane prepolymer (UP) has an oxyethylene unit content of preferably 30 to 90 wt %, more preferably 40 to 80 wt % based on the weight of the NCO-terminated urethane prepolymer (UP), in terms of reactivity.

The NCO-terminated urethane prepolymer (UP) can be obtained by reacting the polyisocyanate component (A) with the polyol component (B).

The usage ratio of the polyisocyanate component (A) to the polyol component (B) in terms of equivalent ratio of the isocyanate group in (A) to the hydroxyl group in (B) (NCO group/OH group) is preferably 1.5 to 3, more preferably 1.8 to 2.3, still more preferably 1.9 to 2.1. With these ranges, the resulting product has a relatively low viscosity and is easily handleable as a sealant, with further improved adhesive strength to reproductive tissue.

Examples of the method of producing the NCO-terminated urethane prepolymer (UP) include a conventionally known method (such as WO 03/051952). For example, in one method, the polyisocyanate component (A) and the polyol component (B) are reacted at 50° C. to 100° C. for 1 to 10 hours. In this case, the polyisocyanate component (A) and the polyol component (B) may be added in advance or may be gradually added dropwise.

The NCO-terminated urethane prepolymer (UP) has a structure with at least two (preferably two) isocyanate groups and without active hydrogen atoms in the molecule.

The isocyanate group in the NCO-terminated urethane prepolymer (UP) is present preferably at a position with less steric hindrance, more preferably a terminal position with less steric hindrance, in terms of reactivity with blood or a body fluid, for example.

The NCO-terminated urethane prepolymer (UP) has an isocyanate group content (the percentage of weight of the isocyanate group in the weight of (UP) as a whole) of preferably 1 to 10 wt %, more preferably 1.2 to 8 wt %, still more preferably 1.5 to 6 wt %. With these ranges, the adhesive strength to reproductive tissue is further improved.

The isocyanate group content can be measured by a method which includes adding an excessive amount of di-n-butylamine solution to a sample for reaction, and performing back titration of unreacted di-n-butylamine with a hydrochloric acid standard solution in accordance with, for example, JIS K 7301:1995, 6.3 "Isocyanate group content rate".

The NCO-terminated urethane prepolymer (UP) has a number average molecular weight (Mn) of preferably 500 to 30,000, more preferably 800 to 20,000, still more preferably 1,000 to 10,000, particularly preferably 1,200 to 8,000. With these ranges, the adhesive strength to reproductive tissue is further improved.

The NCO-terminated urethane prepolymer (UP) has a total content of urethane groups and urea groups of preferably 1 to 20 wt %, more preferably 1 to 15 wt %, still more preferably 2 to 10 wt % based on the weight of the NCO-terminated urethane prepolymer (UP), in terms of adhesive strength to reproductive tissue.

The total content of urethane groups and urea groups in the NCO-terminated urethane prepolymer (UP) can be calculated from the raw material feeding amount.

The NCO-terminated urethane prepolymer (UP) has a fluorine content of preferably 1 to 23 wt %, more preferably 5 to 22 wt %, still more preferably 7 to 20 wt % based on the weight of the NCO-terminated urethane prepolymer (UP). With these ranges, the resulting product has good adhesion to reproductive organs, can prevent amniotic fluid leakage by sealing the reproductive organ, and can also be peeled off without damaging reproductive tissue.

The fluorine content in the NCO-terminated urethane prepolymer (UP) can be calculated from the feed amount of each component used in the production of the NCO-terminated urethane prepolymer (UP). Specifically, the fluorine content can be calculated by the following calculation formula from a fluorine content (L1) (wt %) in the fluorine-containing non-aromatic polyisocyanate compound (A1) used in the production of the NCO-terminated urethane prepolymer (UP) and a percentage (L2) (wt %) of the (A1) relative to the total weight of the polyisocyanate component (A) and the polyol component (B).

Fluorine content (wt %) in NCO-terminated urethane prepolymer (UP)=(L1)×(L2)/100

The sealant for reproductive organs of the present invention may further contain a phenolic radical scavenger (PRS). With the presence of the PRS, it is possible to inhibit time-dependent degradation and decomposition of a sheet-like or sponge-like cured product produced by the reaction of the NCO-terminated urethane prepolymer (UP) with water and to prevent a decrease in adhesive strength to reproductive tissue.

Examples of the phenolic radical scavenger (PRS) include monophenolic, bisphenolic, and polymer phenolic radical scavengers.

Examples of the monophenolic radical scavenger include 2,6-di-t-butyl-p-cresol (e.g., Antage BHT available from Kawaguchi Chemical Industry Co., Ltd.), butylated hydroxy anisole (e.g., Orient BHT available from Orient Chemical Industries Co., Ltd.), 2,6-di-t-butyl-4-ethylphenol (e.g., Noclizer M-17 available from Ouchi-Shinko Chemical Industrial Co., Ltd.), and stearyl-β-(3,5-dit-butyl-4-hydroxyphenyl)propionate (e.g., ADK STAB AO-50 available from Adeka Corporation).

Examples of the bisphenolic radical scavenger include 2,2'-methylenebis(4-methyl-6-t-butylphenol)(e.g., Antage W-400 available from Kawaguchi Chemical Industry Co., Ltd.), 2,2'-methylenebis(4-ethyl-6-t-butylphenol) (e.g., Antage W-500 available from Kawaguchi Chemical Industry Co., Ltd.), 4,4'-butylidenebis(3-methyl-6-t-butylphenol) (e.g., Antage Crystal available from Kawaguchi Chemical Industry Co., Ltd.), 4,4'-thiobis(3-methyl-6-t-butylphenol) (e.g., Antage W-300 available from Kawaguchi Chemical Industry Co., Ltd.), 1,6-hexanediol-bis[3-(3,5-di-t-butyl-4-hydroxyphenyl)propionate] (e.g., Irganox s259 available from Ciba Specialty Chemicals), and 3,9-bis[1,1-dimethyl-2-[β-(3-t-butyl-4-hydroxy-5-methylphenyl)propionyl]ethyl] 2,4,8,10-tetraoxaspiro[5.5]undecane (e.g., ADK STAB AO-80 available from Adeka Corporation).

Examples of the polymer phenolic radical scavenger include tetrakis-[methylene-3-(3',5'-di-t-butyl-4'-hydroxyphenyl)propionate]methane (e.g., Irganox 1010 available from Ciba Specialty Chemicals), 1,3,5-trimethyl-2,4,6-tris (3,5-di-t-butyl-4-hydroxybenzyl)benzene (e.g., ADK STAB AO-330 available from Adeka Corporation), 1,1,3-tris(2-methyl-4-hydroxy-5-t-butylphenyl)butane (e.g., ADK STAB AO-30 available from Adeka Corporation), bis[3,3'-bis-(4'-hydroxy-3'-t-butylphenyl)butyric acid]glycol ester (e.g., antioxidant TMOZ available from Hoechst AG), and 1,3,5-tris(3',5'-di-t-butyl-4'-hydroxybenzyl)-sec-triadine-2,4,6-(1H,3H,5H)trione (e.g., ADK STAB AO-20 available from Adeka Corporation).

The phenolic radical scavenger (PRS) has a molecular weight of preferably 500 to 1200, more preferably 600 to 1100, still more preferably 700 to 1000. With these ranges, the cured body is further less likely to undergo time-dependent degradation and decomposition.

The phenolic radical scavenger (PRS) preferably contains at least two hydroxy groups, more preferably 2 to 5 hydroxy groups, still more preferably 3 or 4 hydroxy groups. With these ranges, the cured body is further less likely to undergo time-dependent degradation and decomposition.

Of these, in order to inhibit time-dependent degradation and decomposition of the cured body, the phenolic radical scavenger is preferably a bisphenolic radical scavenger or a polymer phenolic radical scavenger; more preferably tetrakis-[methylene-3-(3',5'-di-t-butyl-4'-hydroxyphenyl)propionate]methane, 1,1,3-tris(2-methyl-4-hydroxy-5-t-butylphenyl)butane, 1,3,5-trimethyl-2,4,6-tris(3,5-di-t-butyl-4-hydroxybenzyl)benzene, 1,3,5-tris(3',5'-di-t-butyl-4'-hydroxybenzyl)-sec-triadine-2,4,6-(1H,3H,5H)trione, or 1,6-hexanediol-bis[3-(3,5-di-t-butyl-4-hydroxyphenyl)propionate].

Although they are also radical scavengers, the phenolic radical scavengers (PRS) are preferred than non-phenolic radical scavengers (e.g., aromatic amine radical scavengers (such as octylated diphenylamine, N-n-butyl-p-aminophenol, and phenothiazine), sulfur radical scavengers (such as dilauryl-3,3'-thiodipropionate, distearyl-3,3'-thiodipropionate, pentaerythritol tetrakis(3-laurylthiopropionate)), and phosphoric radical scavengers (trisnonylphenyl phosphite, tris(2,4-di-t-butylphenyl)phosphite, and distearyl pentaerythritol diphosphite)). Use of a phenolic radical scavenger (PRS) can inhibit time-dependent degradation and decomposition of a cured body of the NCO-terminated urethane prepolymer (UP), providing excellent adhesive-retaining properties.

The phenolic radical scavenger (PRS) and a radical scavenger other than the PRS may be used in combination.

The phenolic radical scavenger (PRS) content is preferably 0.01 to 3 wt %, more preferably 0.02 to 1 wt %, still more preferably 0.05 to 0.5 wt % based on the weight of the NCO-terminated urethane prepolymer (UP). With these ranges, time-dependent degradation of a cured body can be inhibited, and no adverse effect will be exerted on a human body.

The phenolic radical scavenger (PRS) may be added to the NCO-terminated urethane prepolymer (UP), or may be added to the polyisocyanate component (A) and/or the polyol component (B) in advance to the production of the NCO-terminated urethane prepolymer (UP).

The sealant for reproductive organs of the present invention may contain other components, if necessary, in addition to the NCO-terminated urethane prepolymer (UP) and the phenolic radical scavenger (PRS).

Examples of the other components include medicinal substances having physiological activity (such as medicine for central nerve, medicine for allergy, medicine for a circulatory organ, medicine for a respiratory organ, medicine for a digestive organ, hormonal agents, metabolic agents, antineoplastic agents, antibiotic agents, and chemotherapeutic agents), fillers (such as carbon black, red iron oxide, calcium silicate, sodium silicate, titanium oxide, acrylic resin powder, and various ceramic powders), and plasticizers (such as DBP, DOP, TCP, tributoxyethyl phosphate, and other various esters). When the other components are contained, the amounts thereof are suitably determined depending on use and the like. The other components may also be mixed into the polyisocyanate component (A), the polyol component (B), and/or the phenolic radical scavenger (PRS) in advance for prepolymer reaction, or may be mixed into the NCO-terminated urethane prepolymer (UP) and/or the phenolic radical scavenger (PRS) after reaction.

The cured product (X) of the sealant for reproductive organs of the present invention at 25° C. preferably has a contact angle with water of 60° to 110°, more preferably 72° to 98°, still more preferably 75° to 95°, in terms of adhesion to reproductive tissue.

The contact angle with water is measured not on the surface of the cured product (X) in contact with a glass plate but on the surface in contact with atmosphere, using a contact angle meter ("PD-W" available from Kyowa Interface Science, Inc.).

The contact angle of the cured product (X) with water at 25° C. can be increased by increasing the fluorine content in the NCO-terminated urethane prepolymer (UP), and can be decreased by decreasing the fluorine content in the NCO-terminated urethane prepolymer (UP). Also, the contact angle can be decreased by increasing the oxyethylene unit content in the polyol component (B), and can be increased by decreasing the oxyethylene unit content in the polyol component (B).

The storage modulus G' of the cured product (X) at 25° C. can be increased by increasing the fluorine content in the NCO-terminated urethane prepolymer (UP). The storage modulus G' can be decreased by increasing the oxyethylene unit content in the polyol component (B).

In the NCO-terminated urethane prepolymer (UP) contained in the sealant of the present invention, an isocyanate group reacts with water (e.g., water in the body fluid such as blood and lymph fluid) to produce an amino group and carbon dioxide, and the amino group further reacts with the isocyanate group, increasing the molecular weight (i.e., polymerization is proceeded). The reaction product becomes foam-like (sponge-like) due to the carbon dioxide produced by the reaction, resulting in a flexible foam-containing coating film having good adhesive strength to reproductive tissue.

Thus, the sealant for reproductive organs of the present invention is rapidly polymerized due to water such as amniotic fluid, and exerts a function that prevents amniotic fluid leakage from the uterus (i.e., sealing function). If necessary, for example, a physiological saline solution is sprayed to supply water so that the initial adhesive strength can be increased.

The sealant for reproductive organs of the present invention is preferably used for the cervical canal.

The cervical canal can be sealed, for example, by a method that directly injects the sealant to the cervical canal or a method that injects the sealant using a jig or the like. The sealing method can be suitably selected depending on mucous conditions in the cervical canal, conditions of amniotic fluid leakage, or the like.

The sealant for reproductive organs of the present invention has adequate adhesion to reproductive tissue, so that the sealant can block the cervical canal or the like to inhibit amniotic fluid leakage and can also be peeled off without damaging reproductive tissue. Thus, the sealant can be suitably used to prevent amniotic fluid leakage from the uterus.

EXAMPLES

The present invention is described in more detail below with reference to examples, but the present invention is not limited to these examples. The "part(s)" indicate part(s) by weight, and "%" indicates wt %.

Production Example 1

An autoclave was charged with ethylene glycol (15.5 parts) and potassium hydroxide (3.8 parts). After purging with nitrogen (oxygen concentration in the gas phase: 450 ppm), the mixture was dehydrated in vacuum at 120° C. for 60 minutes.

Subsequently, a mixture of ethylene oxide (784.5 parts) and 1,2-propylene oxide (200 parts) was injected with pressure at 100° C. to 130° C. over about 10 hours, followed by reaction at 130° C. for 3 hours, whereby a liquid-state crude polyether having an oxyethylene unit content of 80% was obtained.

The liquid-state crude polyether (1000 parts) was placed in the autoclave which was purged with nitrogen (oxygen concentration in the gas phase: 450 ppm), followed by addition of ion-exchanged water (30 parts) and then synthesized magnesium silicate (sodium content: 0.2%) (10 parts). After another purging with nitrogen, the mixture was stirred at a stirring rate of 300 rpm at 90° C. for 45 minutes. Next, filtration was performed under nitrogen atmosphere using a glass filter (GF-75 available from Toyo Roshi Kaisha, Ltd.), whereby a random coadduct (B1-1) of ethylene oxide and 1,2-propylene oxide to ethylene glycol was obtained.

The (B1-1) had a number average molecular weight of 4000, an oxyethylene unit content of 80%, and an alkali metal and/or alkaline earth metal content of 0.02 mmol/kg.

Production Example 2

An autoclave was charged with propylene glycol (42.2 parts) and potassium hydroxide (3.8 parts). After purging with nitrogen (oxygen concentration in the gas phase: 450 ppm), the mixture was dehydrated in vacuum at 120° C. for 60 minutes.

Subsequently, a mixture of ethylene oxide (800.0 parts) and 1,2-propylene oxide (157.8 parts) was injected with pressure at 100° C. to 130° C. over about 10 hours, followed by reaction at 130° C. until the volatile content was 0.1% or less, whereby a liquid-state crude polyether was obtained.

The liquid-state crude polyether was treated with synthesized magnesium silicate as in Production Example 1, whereby a random coadduct (B1-2) of ethylene oxide and 1,2-propylene oxide to propylene glycol was obtained.

The (B1-2) had a number average molecular weight of 1800, an oxyethylene unit content of 84%, and an alkali metal and/or alkaline earth metal content of 0.03 mmol/kg.

Production Example 3

An autoclave was charged with propylene glycol (362 parts) and potassium hydroxide (3.8 parts). After purging with nitrogen (oxygen concentration in the gas phase: 450 ppm), the mixture was dehydrated in vacuum at 120° C. for 60 minutes.

Subsequently, 1,2-propylene oxide (632 parts) was injected with pressure at 100° C. to 130° C. over about 10 hours, followed by reaction at 130° C. until the volatile content was 0.1% or less, whereby a liquid-state crude polyether was obtained.

The liquid-state crude polyether was treated with synthesized magnesium silicate as in Production Example 1, whereby a 1,2-propylene oxide adduct (B2-1) to propylene glycol was obtained.

The (B2-1) had a number average molecular weight of 210, an oxyethylene unit content of 0%, and an alkali metal and/or alkaline earth metal content of 0.04 mmol/kg.

Production Example 4

An autoclave was charged with propylene glycol (100 parts) and potassium hydroxide (3.8 parts). After purging with nitrogen (oxygen concentration in the gas phase: 450 ppm), the mixture was dehydrated in vacuum at 120° C. for 60 minutes.

Subsequently, 1,2-propylene oxide (681 parts) was injected with pressure at 100° C. to 130° C. over about 10 hours, followed by reaction at 130° C. until the volatile content was 0.1% or less, whereby a liquid-state crude polyether was obtained.

The liquid-state crude polyether was treated with synthesized magnesium silicate as in Production Example 1, whereby a 1,2-propylene oxide adduct (B2-2) to propylene glycol was obtained. The (B2-2) had a number average molecular weight of 600, an oxyethylene unit content of 0%, and an alkali metal and/or alkaline earth metal content of 0.03 mmol/kg.

TABLE 1

| Polyol component (B) | | Production Example | | | |
|---|---|---|---|---|---|
| | | 1 (B1-1) | 2 (B1-2) | 3 (B2-1) | 4 (B2-2) |
| Feeding amount (parts by weight) | Ethylene glycol | 15.5 | — | — | — |
| | Propylene glycol | — | 42.2 | 362 | 100 |
| | Ethylene oxide | 784.5 | 800.0 | — | — |
| | 1,2-Propylene oxide | 200 | 157.8 | 632 | 681 |
| Number average molecular weight | | 4,000 | 1,800 | 210 | 600 |
| Oxyethylene unit content (wt %) | | 80 | 80 | 0 | 0 |
| HLB | | 16.3 | 17.2 | 14.9 | 7.6 |

Example 1

The random coadduct (B1-1) (86.5 parts) of ethylene oxide and 1,2-propylene oxide obtained in Production Example 1 was used as the polyol component (B). Under nitrogen atmosphere, the (B1-1) was dehydrated under reduced pressure at 100° C. for 2 hours, and then cooled to 50° C. Tetrakis-[methylene-3-(3',5'-di-t-butyl-4'-hydroxyphenyl)propionate]methane (Irganox 1010 available from Ciba Specialty Chemicals) (0.5 parts) was added as a phenolic radical scavenger (PRS) thereto, followed by stirring for 30 minutes to obtain a uniform mixture. The mixture was further cooled to 40° C., and bis(isocyanatomethyl)perfluorobutane (OCN—$CH_2$—$(CF_2)_4$—$CH_2$—NCO) (A1-1) (13.5 parts) (NCO group/OH group ratio=2/1) as the fluorine-containing non-aromatic polyisocyanate compound (A1) was added thereto, followed by stirring to obtain a uniform mixture. The temperature was raised to 80° C., and the mixture was reacted at 80° C. for 6 hours, whereby an NCO-terminated urethane prepolymer (UP-1) of the present invention was obtained, which was used directly as a sealant (1) for reproductive organs.

The (UP-1) had an isocyanate group content of 1.8%. The polyol component (B) had an oxyethylene unit content of 80%, the (UP-1) had an oxyethylene unit content of 69%, and the (UP-1) had a fluorine content of 6.6 wt %.

Examples 2 to 7 and Comparative Examples 1 and 2

NCO-terminated urethane prepolymers (UP-2) to (UP-7), (UP'-1), and (UP'-2) were obtained as in Example 1, except that the compositions shown in Table 2 were used. These products were used as sealants for reproductive organs according to Examples 2 to 7 and Comparative Examples 1 and 2.

TABLE 2

| | | | Example | | | | | | | Comparative Example | |
|---|---|---|---|---|---|---|---|---|---|---|---|
| | | | 1 (UP-1) | 2 (UP-2) | 3 (UP-3) | 4 (UP-4) | 5 (UP-5) | 6 (UP-6) | 7 (UP-7) | 1 (UP'-1) | 2 (UP'-2) |
| NCO-terminated urethane prepolymer (UP) | | | | | | | | | | | |
| Feeding amount (parts by weight) | Hydrophilic polyol (B1) | (B1-1) | 86.5 | 61.8 | 72.3 | 67.2 | 73.8 | — | 60.5 | 83.6 | 34.2 |
| | | (B1-2) | — | — | — | — | — | 55.8 | — | — | — |
| | Another polyol (B2) | (B2-1) | — | 6.9 | — | 7.5 | — | 6.2 | — | 6.2 | 14.7 |
| | | (B2-2) | — | — | 8.1 | — | 8.2 | — | 6.7 | — | — |
| | Fluorine-containing non-aromatic polyisocyanate compound (A1) | (A1-1) | 13.5 | 31.3 | 19.6 | — | 18 | 38 | 32.8 | — | 51.1 |
| | | (A1-2) | — | — | — | 25.3 | — | — | — | — | — |
| | Fluorine atom-free polyisocyanate compound (A2) | (A2-1) | — | — | — | — | — | — | — | 10.2 | — |
| | NCO group/OH group | | 2/1 | 2/1 | 2/1 | 2/1 | 1.8/1 | 2/1 | 4/1 | 2/1 | 2/1 |
| Fluorine content in (UP) (wt %) | | | 6.6 | 15.3 | 9.6 | 12.4 | 8.8 | 18.6 | 16.0 | 0 | 25.0 |
| Isocyanate group content in (UP) (wt %) | | | 1.8 | 4.0 | 2.8 | 4.6 | 2.1 | 5.1 | 6.3 | 2.4 | 6.5 |
| Total content of urethane groups and urea groups in (UP) (wt %) | | | 3.6 | 8.4 | 5.3 | 9.1 | 4.9 | 10.2 | 8.8 | 4.8 | 13.8 |
| Oxyethylene unit content in (B1) (wt %) | | | 80 | 80 | 80 | 80 | 80 | 80 | 80 | 80 | 80 |
| Oxyethylene unit content in (B) (wt %) | | | 80 | 72 | 72 | 72 | 72 | 72 | 72 | 74 | 56 |
| Evaluation results | Storage modulus G' of cured product (X) (kPa) | | 900 | 1,200 | 1,200 | 1,200 | 1,200 | 1,200 | 1,200 | 180 | 2,700 |
| | Contact angle of cured product (X) with water (°) | | 60 | 80 | 70 | 80 | 68 | 97 | 90 | 55 | 115 |
| | Pressure-resistant sealability (kPa) | | 50 | 45 | 45 | 44 | 45 | 42 | 44 | 25 | 15 |
| | Long-term sealing (number of days) | | 14 | 13 | 13 | 13 | 13 | 12 | 13 | 5 | 4 |
| | Peeling test (score) | | 5 | 4 | 5 | 5 | 4 | 4 | 4 | 2 | 3 |

The components in Table 2 are as follows.
(B1-1): random coadduct of ethylene oxide and 1,2-propylene oxide to ethylene glycol obtained in Production Example 1
(B1-2): random coadduct of ethylene oxide and 1,2-propylene oxide to propylene glycol obtained in Production Example 2
(B2-1): 1,2-propylene oxide adduct to propylene glycol obtained in Production Example 3
(B2-2): 1,2-propylene oxide adduct of propylene glycol obtained in Production Example 4
(A1-1): bis(isocyanatomethyl)perfluorobutane (OCN—CH$_2$—(CF$_2$)$_4$—CH$_2$—NCO) having a fluorine atom content of 49 wt %
(A1-2): perfluorotrimethylene diisocyanate (OCN—(CF$_2$)$_3$—NCO) having a fluorine atom content of 49 wt %
(A2-1): hexamethylene diisocyanate having a fluorine atom content of 0 wt %

Evaluation (i) Evaluation of storage modulus G' at 25° C.

Each (1 g) of the sealants for reproductive organs obtained in Examples 1 to 7 and Comparative Examples 1 and 2 was placed on a glass plate (20 cm×26 cm), spread to a coating thickness of 120 to 150 μm using a glass rod, cured by standing at a temperature of 25° C. and a relative humidity of 1 to 10% for 24 hours, and cut to a piece with a width of 5 to 8 mm and a length of 20 to 25 cm, whereby a sample of the cured product (X) was obtained.

The sample was measured to evaluate the storage modulus G' of the cured product (X) at 25° C., using a dynamic viscoelasticity measuring device ("Rheogel-E400" available from UBM) at a measurement temperature of −100° C. to 50° C., a heating rate of 2° C./rain, and a frequency of 11 Hz in a shear mode. Table 2 shows the results.

(ii) Evaluation of contact angle with water at 25° C.

Samples were produced in the same manner as for the measurement of the storage modulus G' at 25° C. described above.

The contact angle of the cured product (X) with water at 25° C. was measured on the surface of each sample in contact with atmosphere, using a contact angle meter ("PD-W" available from Kyowa Interface Science, Inc.). Table 2 shows the results.

(iii) Pressure-resistant sealing test

Each (0.5 g) of the sealants for reproductive organs of Examples 1 to 7 and Comparative Examples 1 and 2 was injected into a porcine cervical canal 12 to seal the opening of a porcine uterus 10. Then, a uterus-oviduct junction 13 was ligated. Subsequently, a physiological saline solution 20 (37° C.) was continuously injected at a speed of 20 mL/sec into the intrauterine cavity through a catheter 21 indwelled on the uterine wall, and the inner pressure of the uterus was measured over time. The inner pressure of the uterus at which leakage of the physiological saline solution 20 was observed from a cervical opening 11 was evaluated as pressure-resistant sealability. Table 2 shows the results.

(iv) Long-term sealing test

Using the cervical opening sealing method used in the pressure-resistant sealing test, 150 mL of the physiological saline solution 20 (37° C.) was accumulated in the porcine uterus 10, and the period (number of days) until leakage of the physiological saline solution 20 occurred from the cervical opening 11 was measured as the long-term sealability. Table 2 shows the results.

(v) Evaluation of tissue damage by peeling

Two pieces of extracted porcine uterus tissue (3 cm (length)×1 cm (width)) were provided. For each of Examples 1 to 7 and Comparative Examples 1 and 2, the sealant for reproductive organs (0.5 g) was applied to one of the pieces to a size of 2 cm (length)×1 cm (width), leaving a 1-cm edge on one side in the longitudinal direction, and the piece was bonded to the other piece, followed by standing at a temperature of 37° C. and a humidity of 80% RH for 2 weeks.

Subsequently, peeling was performed at a tension speed of 5 ram/min using an autograph in accordance with JIS K 6854-3, and the tissue damage on the peeling surface was evaluated under the following criteria. Table 2 shows the results. The tissue damage was evaluated by staining the peeling surface with HE and scoring the tissue.

5: Tissue damage occurred in 0% or more and less than 20% of the entire sample.
4: Tissue damage occurred in 20% or more and less than 40% of the entire sample.
3: Tissue damage occurred in 40% or more and less than 60% of the entire sample.
2: Tissue damage occurred in 60% or more and less than 80% of the entire sample.
1: Tissue damage occurred in 80% to 100% of the entire sample.

The results on Table 2 show that the sealants for reproductive organs of Examples 1 to 7 have high pressure-resistant sealability and can maintain sealing for a long period, and that peeling of the cured products of these sealants causes only small damage to reproductive tissue. Thus, these sealants are excellent sealants for reproductive organs.

INDUSTRIAL APPLICABILITY

The sealant for reproductive organs of the present invention has adequate adhesion to reproductive tissue, can block the cervical canal or the like to inhibit amniotic fluid leakage, and can also be peeled off without damaging reproductive tissue. Thus, the sealant can be suitably used to prevent amniotic fluid leakage from the uterus.

REFERENCE SIGNS LIST 10 porcine uterus
11 cervical opening
12 cervical canal
13 uterus-oviduct junction
20 physiological saline solution
21 catheter

The invention claimed is:
1. A method for sealing a reproductive organ, comprising:
applying a sealant to a reproductive organ,
curing the sealant, and
peeling off the cured sealant from the reproductive organ,
wherein the sealant comprises:
an NCO-terminated urethane prepolymer (UP) that is a reaction product of a polyisocyanate component (A) and a polyol component (B) containing a hydrophilic polyol (B1), wherein the polyisocyanate component (A) comprises a fluorine-containing non-aromatic polyisocyanate compound (A1), and the NCO-terminated urethane prepolymer (UP) has a fluorine content of 1 to 23 wt % based on the weight of the NCO-terminated urethane prepolymer (UP), and when the sealant is spread to a thickness of 120 to 150 μm and cured, a sample of the sealant is obtained as a cured product (X) having a storage modulus G' of 200 to 2,000 kPa at 25° C.

2. The method according to claim 1, wherein the NCO-terminated urethane prepolymer (UP) has an isocyanate group content of 1 to 10 wt % based on the weight of the NCO-terminated urethane prepolymer (UP).

3. The method according to claim 1, wherein the NCO-terminated urethane prepolymer (UP) has a total content of urethane groups and urea groups of 1 to 20 wt % based on the weight of the NCO-terminated urethane prepolymer (UP).

4. The method according to claim 1, wherein the hydrophilic polyol (B1) has an oxyethylene unit content of 30 to 90 wt % based on the weight of the hydrophilic polyol (B1).

5. The method according to claim 1, wherein the polyol component (B) has an oxyethylene unit content of 30 to 90 wt % based on the weight of the polyol component (B).

6. The method according to claim 1, wherein the cured product (X) has a contact angle with water of 60° to 110°.

7. The method according to claim 1, wherein the reproductive organ is a cervical canal.

8. A method for preventing amniotic fluid leakage from a uterus, comprising:
applying a sealant to a uterus,
curing the sealant, and
peeling off the cured sealant from the uterus,
wherein the sealant comprises:
an NCO-terminated urethane prepolymer (UP) that is a reaction product of a polyisocyanate component (A) and a polyol component (B) containing a hydrophilic polyol (B1), wherein the polyisocyanate component (A) comprises a fluorine-containing non-aromatic polyisocyanate compound (A1), and the NCO-terminated urethane prepolymer (UP) has a fluorine content of 1 to 23 wt % based on the weight of the NCO-terminated urethane prepolymer (UP), and
when the sealant is spread to a thickness of 120 to 150 μm and cured, a sample of the sealant is obtained as a cured product (X) having a storage modulus G' of 200 to 2,000 kPa at 25° C. is obtained.

9. The method according to claim 8, wherein the NCO-terminated urethane prepolymer (UP) has an isocyanate group content of 1 to 10 wt % based on the weight of the NCO-terminated urethane prepolymer (UP).

10. The method according to claim 8, wherein the NCO-terminated urethane prepolymer (UP) has a total content of urethane groups and urea groups of 1 to 20 wt % based on the weight of the NCO-terminated urethane prepolymer (UP).

11. The method according to claim 8, wherein the hydrophilic polyol (B1) has an oxyethylene unit content of 30 to 90 wt % based on the weight of the hydrophilic polyol (B1).

12. The method according to claim 8, wherein the polyol component (B) has an oxyethylene unit content of 30 to 90 wt % based on the weight of the polyol component (B).

13. The method according to claim 8, wherein the cured product (X) has a contact angle with water of 60° to 110°.

\* \* \* \* \*